(12) United States Patent
Haynes et al.

(10) Patent No.: US 9,963,501 B2
(45) Date of Patent: May 8, 2018

(54) B CELL LINEAGE BASED IMMUNOGEN DESIGN WITH HUMANIZED ANIMALS

(71) Applicants: Regeneron Pharmaceuticals, Inc., Tarrytown, NY (US); Duke University, Durham, NC (US)

(72) Inventors: Barton Haynes, Durham, NC (US); Garnett Kelsoe, Durham, NC (US); Israel Lowy, Dobbs Ferry, NY (US); Aris I. Baras, Mount Kisco, NY (US); Lynn MacDonald, White Plains, NY (US); John McWhirter, Tarrytown, NY (US); Cagan Gurer, Valhalla, NY (US); Karolina A. Meagher, Tarrytown, NY (US); Andrew J. Murphy, Croton-on-Hudson, NY (US); George D. Yancopoulos, Yorktown Heights, NY (US)

(73) Assignee: REGENERON PHARMACEUTICALS, INC., Tarrytown, NY (US)

(*) Notice: Subject to any disclaimer, the term of this patent is extended or adjusted under 35 U.S.C. 154(b) by 0 days. days.

(21) Appl. No.: 14/174,563

(22) Filed: Feb. 6, 2014

(65) Prior Publication Data
US 2014/0221625 A1  Aug. 7, 2014

Related U.S. Application Data

(60) Provisional application No. 61/761,419, filed on Feb. 6, 2013.

(51) Int. Cl.
*C07K 16/10* (2006.01)
*A01K 67/027* (2006.01)

(52) U.S. Cl.
CPC ...... *C07K 16/1045* (2013.01); *A01K 67/0278* (2013.01); *C07K 16/10* (2013.01); *C07K 16/1018* (2013.01); *A01K 2217/072* (2013.01); *A01K 2227/105* (2013.01); *A01K 2267/01* (2013.01); *G01N 2500/00* (2013.01)

(58) Field of Classification Search
None
See application file for complete search history.

(56) References Cited

U.S. PATENT DOCUMENTS

2002/0106629 A1  8/2002  Murphy et al.
2012/0167237 A1  6/2012  Bradley et al.

FOREIGN PATENT DOCUMENTS

WO  WO 1997/13852 A1  4/1997
WO  WO 2013/052095 A2  4/2013
WO  WO 2014/124156 A1  8/2014

OTHER PUBLICATIONS

Ohno et al., PNAS USA, 1991, 88:10726-10729.*
Hioe et al., PLoS One, 2010, 5(4):1-14.*
Haynes, B.F., et al., "B-cell-lineage immunogen design in vaccine development with HIV-1 as a case study," *Nature Biotechnology*, 2012, 30(5): 423-433.
Klein, F., et al., "Antibodies in HIV-1 Vaccine Development and Therapy," *Science*, Sep. 13, 2013, 341: 1199-1204.
Tarlinton, D., et al., "Diversity Among Memory B Cells: Origin, Consequences, and Utility," *Science*, Sep. 13, 2013, 341: 1205-1211.
International Search Report of International Application No. PCT/US2014/015133, dated Apr. 2, 2014.
PCT/US2014/015133 International Preliminary Report on Patentability dated Aug. 11, 2015.
Munshaw, et al., "SoDA2: a Hidden Markov Model approach for identification of immunoglobulin rearrangements," *Bioinformatics*, vol. 26 No. 7 pp. 867-872 (2010).
Smith, et al., "Phage Display," *Chem. Rev.*, vol. 97 No. 2, pp. 301-410 (1997).
Volpe, et al., "SoDA: implementation of a 3D alignment algorithm for inference of antigen receptor recombinations", *Bioinformatics*, vol. 22 No. 4, pp. 438-444 (2006).
Coico, "The Genetic Basis of Antibody Structure," *Immunology A Short Course*, Fifth Edition, Chapter 6, pp. 79-89, (2003).

* cited by examiner

Primary Examiner — Nicole Kinsey White
(74) Attorney, Agent, or Firm — Yongjin Choi; Alston & Bird LLP

(57) ABSTRACT

Non-human animals with humanized immunoglobulin loci and methods of using them in vaccine design are described, as well as methods for making broadly neutralizing antibodies against infectious agents and pathogens are provided. Non-human animals with humanized immunoglobulin loci used in B-cell-lineage immunogen design in vaccine development are provided, as are methods of carrying out such design.

14 Claims, 9 Drawing Sheets

B CELL LINEAGE BASED IMMUNOGEN DESIGN WITH HUMANIZED ANIMALS

CROSS REFERENCE TO RELATED APPLICATIONS

This application claims the benefit of priority to U.S. Provisional Application No. 61/761,419, filed 6 Feb. 2013, which is incorporated by reference herein in its entirety.

STATEMENT OF GOVERNMENT FUNDING

This invention was made with Government support under Grant No. UM1-AI100645, awarded by the Nation Institute of Health (NIH) and National Institute of Allergy and Infectious Diseases (NIAID). The Government has certain rights in this invention.

FIELD

Methods and compositions for immunogen design using B cell lineage design in non-human animals humanized immunoglobulin loci. Methods and compositions for developing immunogens for making vaccines, employing non-human animals with humanized immunoglobulin loci. Iterative processes of priming and boosting of non-human animals having humanized immunoglobulin loci to identify candidate immunogens for use as vaccines and for generating broadly neutralizing antibodies against infectious agents and pathogens. Development of human vaccines in humanized immunoglobulin animals.

BACKGROUND

Vaccines against human pathogens are sorely needed, but difficult to obtain. Few, if any, suitable methods or systems are available for exposing a human immune system to a human infectious agent or pathogen and obtaining useful information that can be used to design a suitable vaccine that induces immunity in a human subject to the infectious agent or pathogen of interest. It is often not ethical, nor practical, to expose human subjects to immunogens derived from a pathogen or an infectious agent in a protocol for designing a vaccine, and non-human animal systems are typically unsuitable for obtaining useful information about human immunogenicity.

Although humans can develop broadly neutralizing antibodies against infectious agents, and epitopes bound by such antibodies can be identified, the epitopes are paradoxically relatively ineffective as immunogens to induce immunity when used as vaccine candidates. This is because the epitopes recognized by broadly neutralizing antibodies are not the same epitopes that bind early stage antibodies, such as those present on early B cell receptors (BCRs) of the human immunoglobulin naïve repertoire. Thus, vaccinating a human subject with an immunogen that contains the epitope of a broadly neutralizing antibody may only rarely, if at all, result in any significant immunity to the infectious agent in the human subject. That is to say, identifying an important epitope that reacts with a broadly neutralizing antibody is, frequently, useless as a potential vaccine. This significant observation compels the conclusion that B cell clonal development toward mature B cells that express broadly neutralizing antibodies is driven by immunogens that are not identical to the epitope bound by the broadly neutralizing antibody. The problem, it seems, is complex and ties in with early B cell development.

In order to develop a rational process of creating effective vaccines from what is known of B cell development and the human immune response to human infectious agents, a suitable system is needed for the development of candidate vaccines—a system that allows assessment of how the human immune response interacts with immunogens and their variants to ultimately develop a B cell line that produces a broadly neutralizing antibody to an epitope of a human infectious agent or pathogen, and—in the process—to identify an immunogen variant that can serve as a vaccine that can induce broadly neutralizing antibodies in the general human population. The process involves a search for a key immunogen that can prime the naïve human immunoglobulin repertoire and, with judiciously selected boost immunogens, drive the B cell clonal selection process to produce a mature B cell that expresses broadly neutralizing antibodies.

There is a need in the art for compositions and methods for generating vaccines that are suitable for immunizing humans against human infectious agents. There is a need in the art for rational methods for designing immunogens to be used as vaccines in human subjects. There is a need in the art for humanized systems, e.g., humanized animals, that can be used in methods to generate vaccines and vaccine candidates to immunize humans against human infectious agents. There is a need for a non-human platform that can recapitulate a human B cell response, for making vaccines to infectious agents by promoting development of desirable B cells through the use of immunogen variants that will ultimately result in the development of desirable B cells that express broadly neutralizing antibodies against an infectious agent of interest. There is also a need to use humanized animals to further develop broadly neutralizing antibodies to epitopes of infectious agents.

SUMMARY

Compositions and methods are provided for vaccine design using non-human animals comprising humanized immunoglobulin sequences, including iterative processes that comprise employing selected immunogens to develop B cell clones from the naïve repertoire (e.g, immature B cells comprising early B cell receptors) that mature into B cells that produce useful antibodies that selectively bind particular immunogens, wherein one or more of the selected immunogens are employed as vaccines. Compositions and methods are described for generating immune cells (in genetically modified non-human animals) that bind particular immunogens of interest, including developing immune cells from naïve or non-mutated states to mature or hyper-mutated states that specifically bind an infectious agent of interest, and employing one or more immunogens of interest which achieved those steps in a vaccine preparation to develop in a subject in need thereof an immune response to an infectious agent of interest, e.g., to develop an immunity in the subject of interest to the infectious agent of interest, and immune cell populations that express immunoglobulin sequences that bind antigens of interest. Methods for making vaccines using rodents with humanized immunoglobulin sequences are provided.

Compositions and methods are provided for facilitating B cell lineage immunogen design using non-human animals having humanized immunoglobulin loci. Compositions and methods are provided for using the non-human animals to identify, through intermediate ancestor B cells and B cells bearing unmutated receptors (e.g., a naïve B cell repertoire, or a B cell repertoire characterized by germline rearrangements that have not been mutated, or have not been somatically hypermutated), immunogens to develop vaccines against infectious agents, which will elicit production from a human immunoglobulin repertoire of mature B cells that express broadly neutralizing antibodies. Compositions and methods are provided for prime and boost cycles using variants of immunogens and, optionally, adjuvants that generate broadly neutralizing antibodies, such that immunogen variants capable of stimulating an early or naïve human B cell repertoire (e.g., a repertoire reflecting germline rearrangements) are identified, wherein the immunogen variants induce the production of a broadly neutralizing antibody against the infectious immunogen.

General methods for making vaccines against human infectious agents and pathogens in non-human animals having humanized immunoglobulin loci are provided.

Compositions and methods for using non-human animals having restricted immunoglobulin repertoires (e.g., a restricted human heavy chain repertoire) are also provided.

In one aspect, methods and compositions are provided using B Cell Lineage-based immunogen design in non-human animals comprising a humanized immunoglobulin locus (e.g., the VELOCIMMUNE® humanized mouse) for iterative development of vaccine immunogens for infectious diseases.

In one embodiment, infectious disease agent components are used as antigen-specific labels to identify precursors of protective antibodies in unimmunized or uninfected VELOCIMMUNE® humanized mice or using similar reagents and related strategies to identify immunogen-induced clonal lineages of anti-infectious agent antibodies that are developing in the desired direction. These antibodies are then made to use as templates for iterative vaccine design, wherein a series of novel immunogens and, optionally, adjuvants to drive an otherwise subdominant or disfavored B cell maturation pathway to become dominant is determined. In one embodiment, sufficient plasma and tissue levels of antibody are made to be protective in the setting of vaccination.

In one aspect, non-human animals comprising humanized immunoglobulin loci (e.g., VELOCIMMUNE® humanized mice) are used to design of vaccine immunogens comprising: employing pre-immune unvaccinated mouse bone marrow to isolate antigen-specific naïve B cells that bind to antigen-specific infectious agent reagents bearing broadly neutralizing epitopes; the antibodies reflective of the naïve B Cell Receptors (BCR) are isolated and made recombinantly; and immunogens are selected for their high affinity binding to these BCR in order to discover immunogens that would selectively drive desired broadly neutralizing B cell lineages to mature in peripheral lymph nodes and spleen.

In one aspect, non-human animals comprising humanized immunoglobulin loci (e.g., VELOCIMMUNE® humanized mice) are vaccinated with existing immunogens that themselves are antigenic for broadly neutralizing antibodies one is trying to induce; the antibodies induced are then isolated by making monoclonal antibodies from the spleens or lymph nodes of the immunized mice; the antibodies are made recombinantly; and then the most mature antibodies in the desired lineage used as a template to further drive the desired lineage to full expression of the desired function, e.g., a protective effector function against an infectious agent. In one embodiment, the protective function includes virus neutralization, antibody-dependent cellular cytotoxicity against infectious agent-infected cells, prevention of movement of infectious agent across mucosal barriers, and blocking of entry of infectious agent in cell targets.

In one aspect, a method is provided for obtaining an immunogen that results in production in a non-human animal comprising a humanized Ig locus of a broadly neutralizing antibody against an infectious agent, comprising iterating and screening candidate immunogens for B cell lineage vaccine design, wherein the iterating and screening comprises:

(a) identifying a first epitope that binds a broadly neutralizing antibody of an infectious agent;

(b) designing a second epitope that specifically binds a first intermediate ancestor antibody of the broadly neutralizing antibody, wherein the second epitope is not identical to the first epitope;

(c) designing a third epitope that specifically binds a second intermediate ancestor antibody of the broadly neutralizing antibody, wherein the third epitope is not identical to the second epitope; and, (d) employing the third epitope as a vaccine against the infectious agent.

in one embodiment, the method further comprises designing a fourth epitope that specifically binds a third intermediate ancestor antibody of the broadly neutralizing antibody, wherein the fourth epitope is employed as a vaccine against the infectious agent.

In one embodiment, the method further comprises designing a fifth epitope that specifically binds a fourth intermediate ancestor antibody of the broadly neutralizing antibody, wherein the fifth epitope is employed as a vaccine against the infectious agent.

In one embodiment, the first, second, third, fourth, or fifth epitope binds an unmutated ancestor antibody. In one embodiment, the first, second, third, fourth, or fifth epitope that binds the unmutated ancestor antibody is employed as a vaccine against the infectious agent.

In one embodiment, the unmutated ancestor antibody is an antibody of a naive B cell. In one embodiment, the unmutated ancestor antibody is displayed on an early B cell as an IgM antibody. In one embodiment, the unmutated ancestor antibody comprises a rearrangement of germline gene segments prior to class switching.

In one aspect, a method for making a vaccine against an infectious agent in a non-human animal that comprises a humanized immunoglobulin locus is provided, comprising priming and boosting with variants of an epitope of the infectious agent, wherein the epitope of the infectious agent binds to a broadly neutralizing antibody. In one embodiment, the priming and boosting with variants of the epitope of the infectious agent is continued until a variant is found that, upon immunizing a naïve non-human animal with a humanized Ig locus, the variant produces a broadly neutralizing antibody. In one embodiment, the variant that produces a broadly neutralizing antibody is employed as a vaccine against the infectious agent.

In one aspect, a method for designing a broadly neutralizing antibody (BNAb) in a non-human animal comprising a humanized immunoglobulin locus is provided, comprising exposing the animal to a first structural variant of an epitope of an immunogen that binds a broadly neutralizing antibody, allowing the animal to develop a first immune response to the first structural variant, and screening antibodies in the animal to obtain a broadly neutralizing antibody against the immunogen. In one embodiment, the method comprises exposing the animal to a second structural variant of the epitope that binds the broadly neutralizing antibody, allowing the animal to develop a second immune response, and screening antibodies from the animal to obtain a broadly neutralizing antibody against the immunogen, wherein the immunogen, the first structural variant, and the second structural variant are not identical.

In one aspect, a method is provided for employing a non-human animal comprising a humanized immunoglobulin locus in an algorithm to determine an unmutated ancestor antibody, comprising administering to the non-human animal a first variant of an immunogen that binds a broadly neutralizing antibody. In one embodiment, the algorithm employs quantitative inference based on the number of different VDJ combinations (roughly $10^9$) compared with the number of possible nucleotide sequences of comparable length (roughly $4^{350}$). The algorithm infers back from the sequence of the broadly neutralizing antibody to the most plausible ancestor, or ancestors.

In one embodiment, the unmutated ancestral VDJ is determined by modeling the somatic mutation rates, the probability that a given nucleotide will be in a mutated states, and the number of passages through somatic hypermutation. See, e.g., Haynes et al. (2012) B-cell-lineage immunogen design in vaccine development with HIV-1 as a case study, Nature Biotech. 30(5):423-433 (hereby incorporated by reference, see, e.g., especially Box 4).

In one aspect, a method is provided for employing a non-human animal with a humanized immunoglobulin locus to optimize and validate immunogens to develop a vaccine against an infectious agent, comprising priming and boosting the non-human animal with an immunogen of interest for B cell lineage vaccine design. In one embodiment, the non-human animal is primed and boosted with a first preselected immunogen, a second pre-selected immunogen, and an nth pre-selected immunogen, until the non-human animal expresses a broadly neutralizing antibody against the infections agent. In one embodiment, the first pre-selected immunogen, the second pre-selected immunogen, or the nth pre-selected immunogen is an effective vaccine against the infectious agent. In one embodiment, nth refers to third, fourth, fifth, sixth, seventh, eighth, ninth, or tenth.

In one aspect, a method is provided for making a vaccine that elicits production in a human subject of a broadly neutralizing antibody against an infectious agent of interest, comprising priming and boosting a non-human animal comprising a humanized Ig locus with variants of an epitope of the infectious agent that binds a broadly neutralizing antibody, wherein a priming and boosting process employing variants of the epitope of the infectious agent that do not bind the broadly neutralizing antibody, but produce in the non-human animal a broadly neutralizing antibody that binds the infectious agent of interest.

In one aspect, a method is provided for making a vaccine that elicits in a human a broadly neutralizing antibody against an infectious agent of interest, comprising identifying an antibody that broadly neutralizes the infectious agent of interest, making variants of the epitope bound by the broadly neutralizing antibody, performing prime and boost cycles with variants of the epitope bound by the broadly neutralizing antibody until an effective variant results in production of an antibody that broadly neutralizes the infectious agent of interest, and employing the effective variant as a vaccine against the infectious agent of interest.

In one aspect, a method for B cell lineage-based vaccine design is provided, comprising: (a) immunizing a non-human animal that comprises a humanized immunoglobulin locus with a first immunogen of interest, wherein the first immunogen of interest comprises a plurality of epitopes; (b) allowing the non-human animal to mount an immune response to the first immunogen of interest, wherein the immune response comprises creating non-human B cells that express human immunoglobulin heavy chain VDJ and human immunoglobulin light chain VJ domains; (c) isolating clonally related memory B cells from the non-human animal that specifically bind a first epitope of interest on the first immunogen of interest; (d) determining VDJ and VJ sequence information for the VDJ and VJ sequences of the memory B cells; (e) employing the determined VDJ and VJ sequence information to determine an unmutated B cell receptor (BCR) VDJ and VJ sequence and, optionally, one or more intermediate ancestor VDJ and VJ sequences between the BCR and the memory B cell; and, (f) making a second immunogen with enhanced affinity (as compared with the first immunogen) to the BCR and/or an intermediate ancestor antibody, wherein the second immunogen is employable in a human subject as a vaccine against the first immunogen of interest.

In one embodiment, the first immunogen of interest is, or is derived from, an infectious agent or a pathogen. In one embodiment, the infectious agent or pathogen is a virus, a bacterium, a fungus, or a parasite. In one embodiment, the infectious agent is selected from HIV-1, hepatitis C, dengue fever virus, and HPV.

In one embodiment, the first immunogen of interest is a protein or a peptide and the second immunogen of interest is a structural variant of the first immunogen of interest. In one embodiment, the structural variant comprises a substitution of one or more amino acids of the protein or peptide. In one embodiment, the first immunogen is a protein with a posttranslational modification (e.g., glycosylation, or presence of a non-protein group, e.g., a lipid), and the second immunogen of interest is a variant of the posttranslational modification.

In one embodiment, the VDJ is derived from a human $V_H$1-69 gene segment and a human D and a human J segment.

In one aspect, a method for designing a vaccine against an infectious agent or pathogen is provided, comprising employing a non-human animal that comprises a humanized immunoglobulin locus as a In one aspect, broadly neutralizing antibodies of interest as used herein are antibodies that exist in human subjects who are infected with an infectious agent of interest, wherein the antibodies are capable of neutralizing the infectious agent in culture. In one embodiment, the antibodies are capable of preventing infection of a cell that said infectious agents can normally infect in the absence of the antibodies.

In various aspects, the infectious agent or pathogen is selected from a virus (e.g., human immunodeficiency virus (HIV), e.g., HIV-1, an influenza virus strain, human papillomavirus (HPV), hepatitis C, hepatitis B, hepatitis A, dengue), a bacterium, a fungus, a parasite (e.g., a malaria strain or species). etc.

In one aspect, a non-human animal comprising a humanized immunoglobulin locus is provided, wherein the animal is immunized with a variant of an epitope of an infectious agent to which a first broadly neutralizing human antibody binds, and wherein the animal as the result of the immunization with the epitope variant comprises a second broadly neutralizing antibody that broadly neutralizes the same epitope of the same infectious agent, wherein the second broadly neutralizing antibody is not identical to the first broadly neutralizing antibody.

Compositions and methods are provided for identifying immunogens for use as vaccines against infectious agents, and for developing broadly neutralizing antibodies against infectious agents, using non-human animals comprising a humanized immunoglobulin locus that express a B cell population derived from the entire human heavy chain variable gene repertoire, operably linked to a plurality of human D segments and a plurality of human J segments; wherein the variable segments are operably linked to a constant region, e.g., a human or non-human constant region on a transgene, or an endogenous non-human constant region operably linked at the endogenous non-human locus to the human heavy chain repertoire. In various embodiments the non-human animal comprises a full and unrearranged human κ and/or λ light chain variable repertoire, on a transgene linked to a human or rodent (e.g., mouse or rat) constant region gene, or at an endogenous non-human light chain locus operably linked to a rodent (e.g., mouse or rat) constant region gene.

Compositions and methods are provided for identifying immunogens for use as vaccines against infectious agents, and for developing broadly neutralizing antibodies against infectious agents, using non-human animals comprising a humanized immunoglobulin locus that express a B cell population derived from no more than one, or no more than two, heavy chain variable region family members (e.g., $V_H$1-69 and/or its polymorphs; $V_H$1-2 and/or its polymorphs) operably linked to a plurality of human D segments and a plurality of human J segments; wherein the variable segments are operably linked to a constant region, e.g., a human or non-human constant region on a transgene, or an endogenous non-human constant region operably linked at the endogenous non-human locus to the restricted human $V_H$ repertoire. In various embodiments the non-human animal comprises a full and unrearranged human κ and/or λ light chain variable repertoire, on a transgene linked to a human or rodent (e.g., mouse or rat) constant region gene, or at an endogenous non-human light chain locus operably linked to a rodent (e.g., mouse or rat) constant region gene.

Genetically modified non-human animals are provided that are immunized with human infectious agents, wherein the non-human animals comprise unrearranged human immunoglobulin variable region gene segments that are capable of rearranging and forming genes that encode variable region sequences operably linked to endogenous non-human constant regions, wherein the variable domains encoded by the sequences specifically bind the infectious agent. In one embodiment, the non-human animal is immunized with an immunogen that is a variant of an immunogen that binds a broadly neutralizing human antibody, e.g., a broadly neutralizing antibody isolated from a patient infected with the infectious agent). In one embodiment, the immunogen that the non-human animal is immunized with is not identical to the immunogen that binds the broadly neutralizing antibody.

In one aspect, a non-human animal with a humanized immunoglobulin heavy chain variable region gene locus and a humanized light chain variable region gene locus is employed to screen for (or use in prime and boost cycles) immunogens to employ as vaccines against human infectious agents or pathogens. In one embodiment, the immunogens are derived from, but are not identical to, immunogens that bind broadly neutralizing antibodies against the infectious agent or pathogen. In one embodiment, the identity of the screening immunogen is about 98%, 97%, 96%, 95%, 90%, 85%, 80%, 75%, 70%, 65%, or 60% identical to the immunogen that binds the broadly neutralizing antibody.

In various aspects, the non-human animals comprising a humanized immunoglobulin locus comprises, e.g., an insertion of one or more unrearranged human heavy chain V, D, and J and/or unrearranged human light chain V and J gene segments, either on a transgene (fully human or human variable/non-human constant) or operably linked to a non-human constant region at an endogenous non-human locus.

In various embodiments, the genetically modified heavy chain locus comprises an endogenous Adam6a gene, Adam6b gene, or both, and the genetic modification does not affect the expression and/or function of the endogenous Adam6a gene, Adam6b gene, or both.

In various embodiments, the non-human animal comprises an ectopically present Adam6a gene, Adam6b gene, or both. In one embodiment, the Adam6a gene is a non-human Adam6a gene. In one embodiment, the Adam6a gene is a mouse Adam6a gene. In one embodiment, the Adam6a gene is a human Adam6a gene. In one embodiment, the Adam6b gene is a non-human Adam6b gene. In one embodiment, the Adam6b gene is a mouse Adam6b gene. In one embodiment, the Adam6b gene is a human Adam6b gene.

In various embodiments, the one or more unrearranged human heavy chain V, D, and J and/or unrearranged human light chain V and J gene segments are present in a restricted repertoire, e.g., the number of human heavy and/or light gene segments present in the non-human animal is less than a complete human repertoire of the corresponding gene segments. In various aspects, the human gene segments are inserted at an endogenous locus (directly or through a recombinase-containing cassette), and endogenous unrearranged gene segments are retained in the genome of the non-human animal. In a specific embodiment, the human gene segments are inserted between the 3'-most non-human gene segment and the first non-human constant gene. In some embodiments where endogenous non-human variable gene segments are present, they are inactivated, e.g., by an inversion or a partial deletion.

In one aspect, the non-human animal is a rodent, e.g., a mouse or a rat.

In one aspect, the non-human animal comprises a plurality of unrearranged human light chain V and J gene segments operably linked to a constant region (e.g., a human or non-human constant region, at an endogenous Ig locus or on a transgene), and the unrearranged human heavy chain locus is restricted to no more than one, or no more than two, or no more than three $V_H$ gene segments operably linked to one or more human D segments and one or more human J segments, at an endogenous Ig locus or on a transgene.

In one aspect, the non-human animal is a mouse or rat that comprises a germline modification resulting in no more than one, no more than two, or no more than three human $V_H$ gene segments operably linked to a plurality of human D and a plurality of human J gene segments, wherein the mouse or rat comprises a plurality of unrearranged human Vκ and Jκ and/or human Vλ and Jλ gene segments operably linked to a human or a non-human constant region gene. In one embodiment, the plurality of unrearranged human Vκ and Jκ and/or human Vλ and Jλ gene segments are operably to endogenous constant region genes at an endogenous non-human light chain locus.

In one aspect, a method is provided for obtaining a broad spectrum antibody against an antigen of interest, comprising:

(a) priming a non-human animal by administering a first immunogen derived from the antigen of interest, wherein the non-human animal comprises:

(i) a genetically modified immunoglobulin heavy chain locus comprising one or more human $V_H$ gene segments, a plurality of human $D_H$ gene segments, and a plurality of human J segments, wherein the $V_H$, $D_H$, and $J_H$ gene segments are operably linked to a heavy chain constant region nucleic acid sequence, (ii) a genetically modified immunoglobulin light chain locus comprising one or more human Vκ gene segments and one or more human Jκ gene segments, wherein the Vκ and the Jκ gene segments are operably linked to a light chain constant region nucleic acid sequence, and wherein the first immunogen comprises a plurality of epitopes;

(b) allowing the non-human animal to mount an immune response against the first immunogen, wherein the immune response comprises generation of non-human B cells that express human immunoglobulin heavy chain (IgH) VDJ and human immunoglobulin light chain (IgL) VJ sequences;

(c) isolating clonally related B cells from the non-human animal that express a B cell receptor (BCR) that specifically binds a first epitope of the first immunogen;

(d) obtaining IgH VDJ and IgL VJ amino acid sequences expressed by the B cell receptor (BCR) of the clonally related B cells;

(e) deducing from the IgH VDJ and IgL VJ sequences unmutated B cell receptor (BCR) VDJ and VJ amino acid sequences, and one or more intermediate ancestor B cell receptor (BCR) VDJ and VJ amino acid sequences expressed by B cells at an intermediate stage of differentiation; and (f) designing a plurality of immunogens that bind with enhanced affinity to the unmutated B cell receptor (BCR) or the intermediate ancestor B cell receptor (BCR);

(g) boosting the immune response in the non-human animal by administering to the non-human animal a second immunogen selected from the plurality of the immunogens in (f), wherein the second immunogen comprises a second epitope distinct from the first epitope; and (h) obtaining the broad spectrum antibody from the non-human animal of (g).

In one embodiment, the immune response of the non-human animal is boosted by serially administering the plurality of immunogens identified in step (e) until the broad spectrum antibody is produced by the non-human animal.

In one embodiment, the immune response of the non-human animal is boosted by administering a combination of the plurality of the immunogens identified in step (e).

In one embodiment, the antigen of interest is, or is derived from, an infectious agent or a pathogen, and the broad spectrum antibody is a broadly neutralizing antibody against the infectious agent or the pathogen.

In one embodiment, the infectious agent or pathogen is selected from the group consisting of a virus, a bacterium, a fungus, and a parasite.

In one embodiment, the infectious agent is selected from the group consisting of a human immunodeficiency virus (HIV), a hepatitis A virus, a hepatitis B virus, a hepatitis C virus, a dengue fever virus, and a human papillomavirus (HPV).

In one embodiment, all, or substantially all, functional endogenous $V_H$ $D_H$, and $J_H$ gene segments in the immunoglobulin heavy chain locus have been deleted or rendered non-functional, and wherein the genetically modified immunoglobulin heavy chain locus comprises a single human $V_H$ gene segment or a polymorphic variant thereof, one or more human $D_H$ gene segment, and one or more human $J_H$ gene segment.

In one embodiment, the genetically modified heavy chain locus comprises an endogenous Adam6a gene, Adam6b gene, or both, and the genetic modification in the heavy chain locus does not affect the expression or function of the endogenous Adam6a gene, Adam6b gene, or both.

In one embodiment, the non-human animal comprises an ectopically present Adam6a gene, Adam6b gene, or both.

In one embodiment, the single human $V_H$ gene segment is selected from the group consisting of $V_H1$-2, $V_H1$-3, $V_H1$-8, $V_H1$-18, $V_H1$-24, $V_H1$-45, $V_H1$-46, $V_H1$-58, $V_H1$-69, $V_H2$-5, $V_H2$-26, $V_H2$-70, $V_H3$-7, $V_H3$-9, $V_H3$-11, $V_H3$-13, $V_H3$-15, $V_H3$-16, $V_H3$-20, $V_H3$-21, $V_H3$-23, $V_H3$-30, $V_H3$-30-3, $V_H3$-30-5, $V_H3$-33, $V_H3$-35, $V_H3$-38, $V_H3$-43, $V_H3$-48, $V_H3$-49, $V_H3$-53, $V_H3$-64, $V_H3$-66, $V_H3$-72, $V_H3$-73, $V_H3$-74, $V_H4$-4, $V_H4$-28, $V_H4$-30-1, $V_H4$-30-2, $V_H4$-30-4, $V_H4$-31, $V_H4$-34, $V_H4$-39, $V_H4$-59, $V_H4$-61, $V_H5$-51, $V_H6$-1, $V_H7$-4-1, $V_H7$-81 gene segment, and a polymorphic variant thereof.

In one embodiment, the single human $V_H$ gene segment is a human $V_H1$-69 gene segment or a polymorphic variant thereof.

In one embodiment, the single human $V_H$ gene segment is a human $V_H1$-2 gene segments or a polymorphic variant thereof.

In one embodiment, the single human $V_H$ gene segment is a human $V_H$ 4-59 gene segment or a polymorphic variant thereof.

In one embodiment, the non-human animal is a rodent.

In one embodiment, the non-human animal is a mouse or a rat.

In one embodiment, the constant region nucleic acid sequence is a human or a rodent nucleic acid sequence.

In one embodiment, the non-human animal is a mouse and the constant region nucleic acid sequence is a mouse constant region nucleic acid sequence.

In one embodiment, all, or substantially all, functional endogenous $V_H$ $D_H$, and $J_H$ gene segments in the immunoglobulin heavy chain locus have been rendered non-functional, and the human $V_H$, $D_H$, and $J_H$ gene segments are present on a transgene.

In one embodiment, the human $V_H$, $D_H$, and $J_H$ gene segments are operably linked to an endogenous constant region nucleic acid sequence at an endogenous non-human immunoglobulin heavy chain locus.

In one embodiment, the genetically modified immunoglobulin light chain locus comprises a replacement of all, or substantially all, functional Vκ gene segments, Jκ gene segments with one or more human Vκ gene segments and one or more Jκ gene segments, wherein the human Vκ gene segments and the Jκ gene segments are operably linked to a light chain constant region nucleic acid sequence.

In one embodiment, the non-human animal comprises a replacement at the endogenous non-human immunoglobulin Vκ locus of all or substantially all functional endogenous Vκ gene segments with human Vκ gene segments selected from Vκ4-1, Vκ5-2, Vκ7-3, Vκ2-4, Vκ1-5, Vκ1-6, Vκ3-7, Vκ1-8, Vκ1-9, Vκ2-10, Vκ3-11, Vκ1-12, Vκ1-13, Vκ2-14, Vκ3-15, Vκ1-16, Vκ1-17, Vκ2-18, Vκ2-19, Vκ3-20, Vκ6-21, Vκ1-22, Vκ1-23, Vκ2-24, Vκ3-25, Vκ2-26, Vκ1-27, Vκ2-28, Vκ2-29, Vκ2-30, Vκ3-31, Vκ1-32, Vκ1-33, Vκ3-34, Vκ1-35, Vκ2-36, Vκ1-37, Vκ2-38, Vκ1-39, Vκ2-40, and a combination thereof.

In one embodiment, the non-human animal comprises a replacement at the endogenous non-human immunoglobulin Jκ locus of all or substantially all functional endogenous non-human immunoglobulin Jκ gene segments with human Jκ gene segments selected from Jκ1, Jκ2, Jκ3, Jκ4, Jκ5, and a combination thereof.

In one embodiment, the one or more human Vκ and Jκ segments are operably linked to an endogenous light chain constant region nucleic acid sequence at an endogenous non-human locus.

In various aspects, broad spectrum antibodies obtainable by any of the methods described herein are provided.

In various aspects, broadly neutralizing antibodies against an infectious agent or a pathogen obtainable by any of the methods described herein are provided.

Further methods and compositions are described in the Detailed Description herein, including but not limited to further descriptions of B-cell-lineage immunogen design, and further descriptions of non-human animals with humanized immunoglobulin loci, all of which can be used in conjunction with any of the aspects or embodiments described herein, unless otherwise indicated or unless the context dictates otherwise.

DETAILED DESCRIPTION

Glossary

Figure 1:
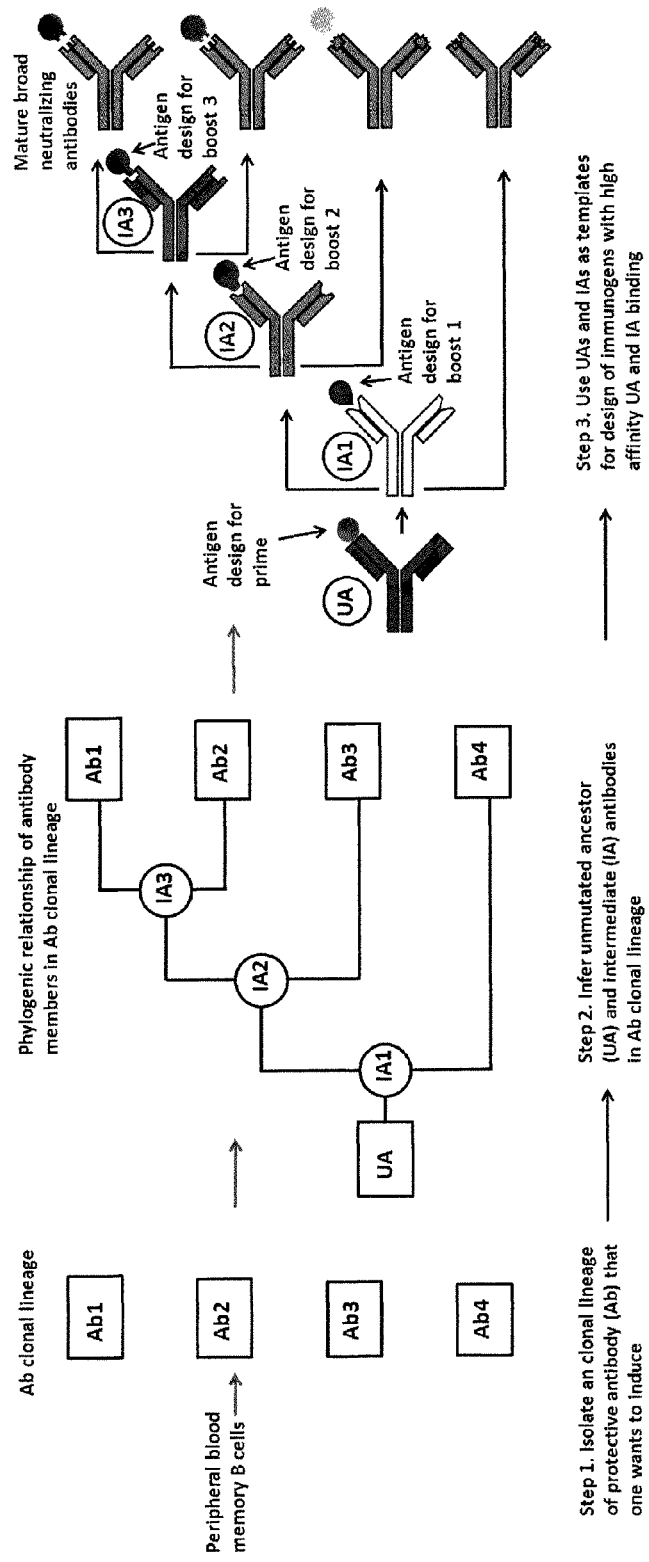
FIG. 1 illustrates general steps of the B cell lineage design-based approach to vaccine design. In the first step, the Ab1, Ab2, Ab3, and Ab4 refer to four different antibody clonal lineages from peripheral blood memory B cells, one or more of which produces a protective antibody that is desired to be induced. Step 2 involves inference of an unmutated ancestor (UA) and intermediate (IA) antibodies in an antibody clonal lineage. Step 3 involves suing the UA(s) and IAs as templates to design immunogens with high affinity US and IA binding. This schematic illustrates a general scheme for regressing from an epitope of an infectious agent that binds a mature, broadly neutralizing antibody to an unmutated ancestor B cell (e.g., UA) that binds a priming immunogen. Through B cell development the UA develops into an IA that binds an antigen for boosting, a process that is iterated until the mature broadly neutralizing antibody is obtained. The iterative process allows for identification of suitable immunogens (antigens for prime and boosting) that may serve in the design of vaccines to elicit mature broadly neutralizing antibodies. See, Haynes et al. (2012) B-cell-lineage immunogen design in vaccine development with HIV-1 as a case study, Nature Biotech. 30(5): 423-433.
Figure 2:
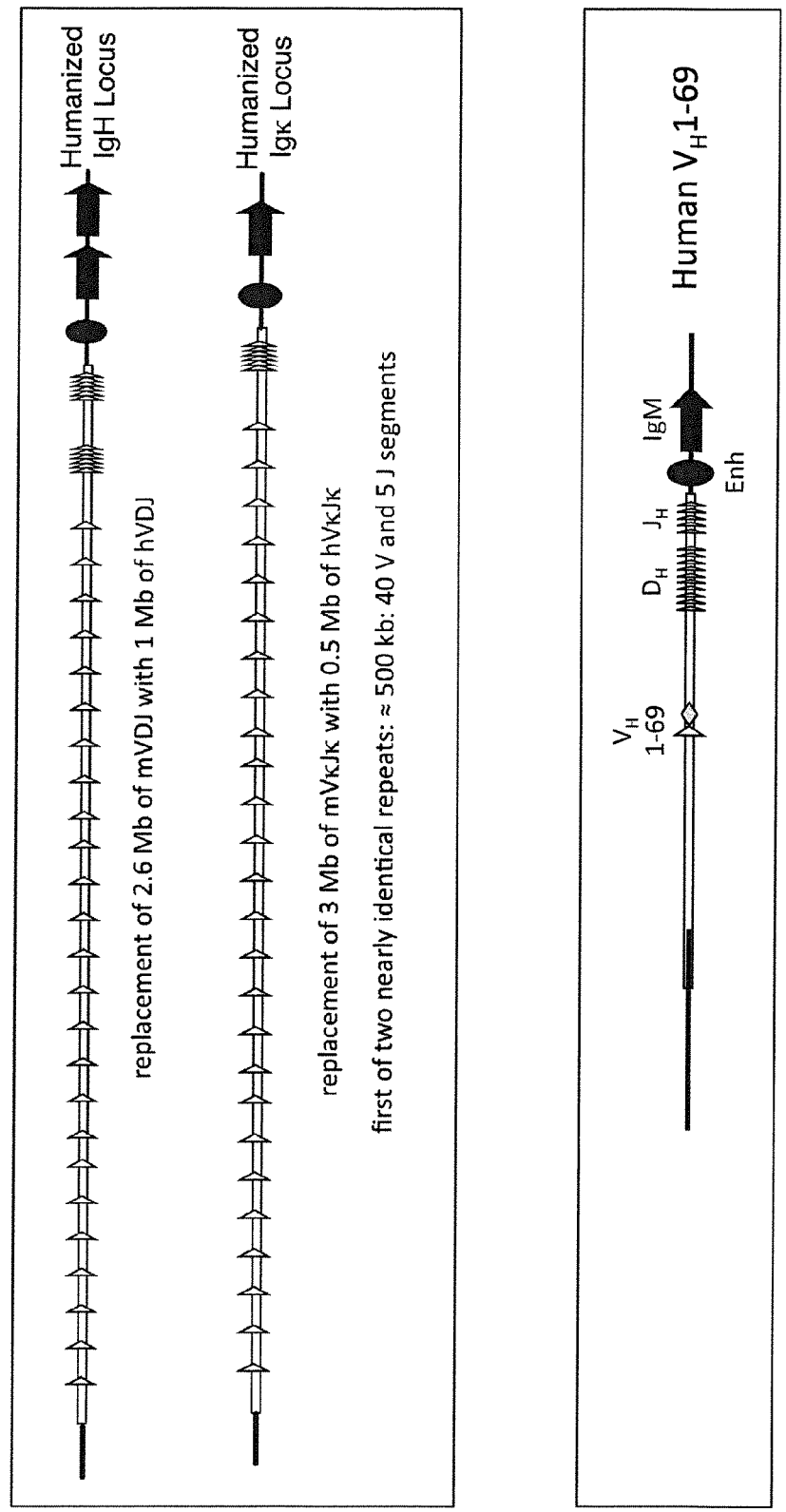
FIG. 2 lists two types of VELOCIMMUNE® humanized mice that can be used for this approach. Top panel: a VELOCIMMUNE® humanized mouse with a replacement of mouse endogenous sequences (closed symbols) with human genomic sequences (closed symbols); Bottom panel: a $V_H$ restricted VELOCIMMUNE® humanized mouse with a single $V_H$1-9 gene segment replacing all endogenous mouse $V_H$ gene segments, operably linked to human D and human J gene segments; for simplicity, the humanized κ locus is not shown for the Human $V_H$1-69 panel. Other $V_H$ restricted VELOCIMMUNE® humanized mice can similarly be used.
Figure 3A:
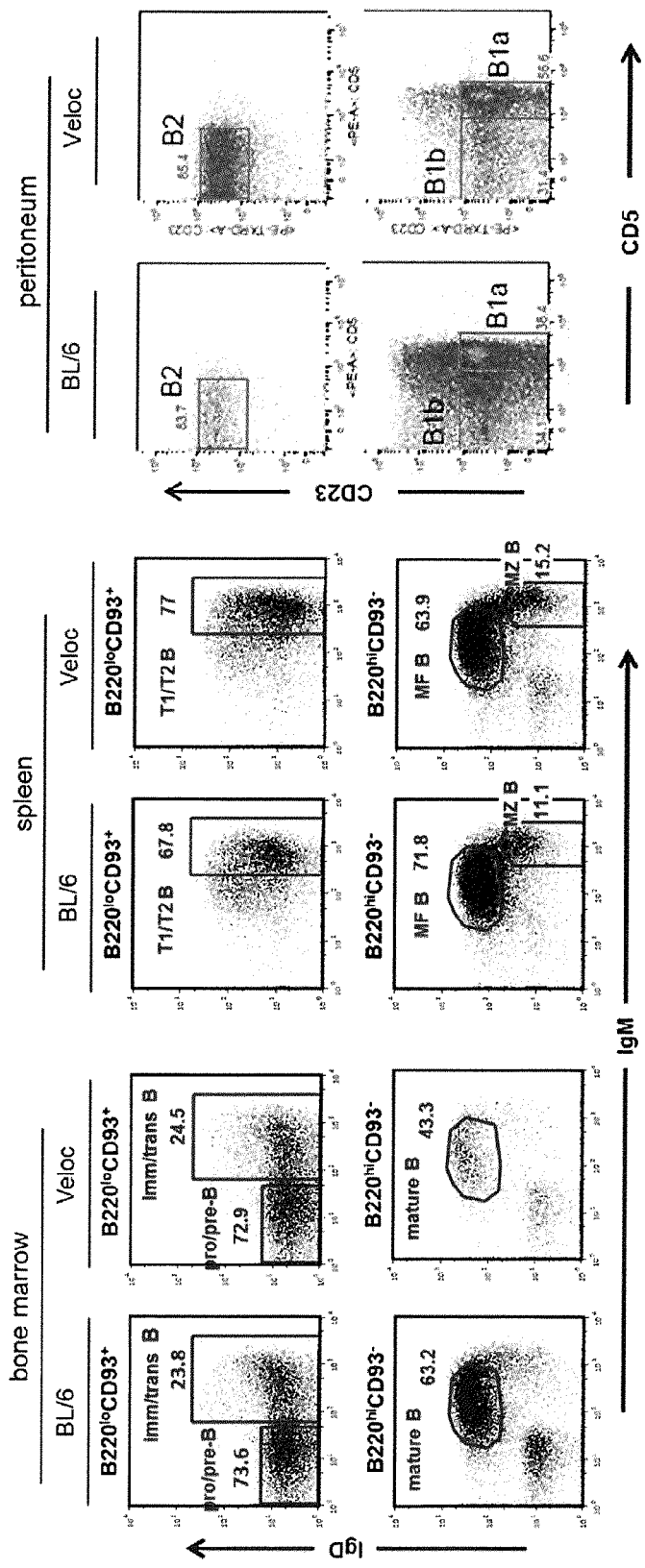
FIG. 3A shows normal B cell subsets of immune cells in VELOCIMMUNE® humanized mice in bone marrow, spleen, and peritoneum, as compared with wild-type BL/6 mice.
Figure 3B:
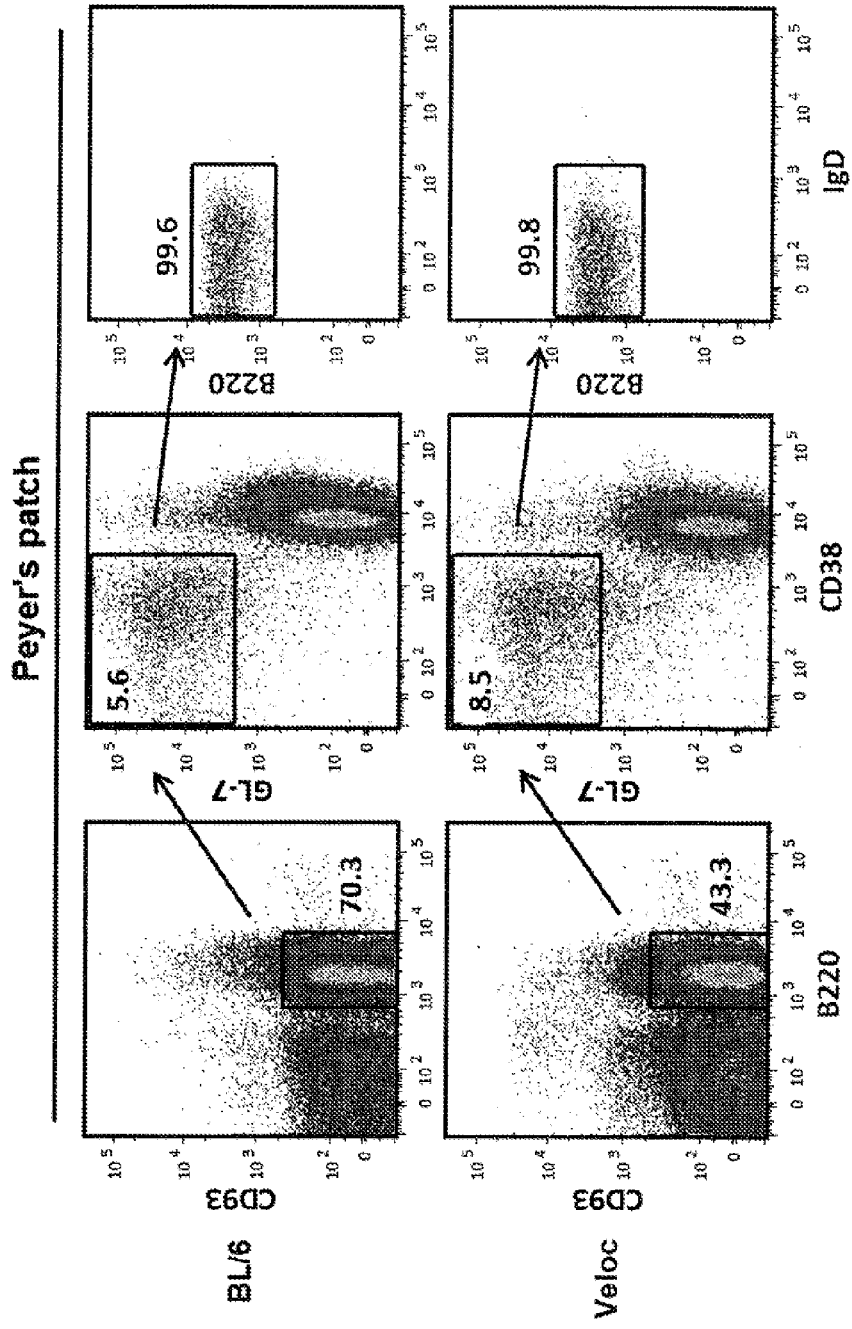
FIG. 3B shows normal B cell subsets of immune cells in VELOCIMMUNE® humanized mice in Peyer's patch.
Figure 4:
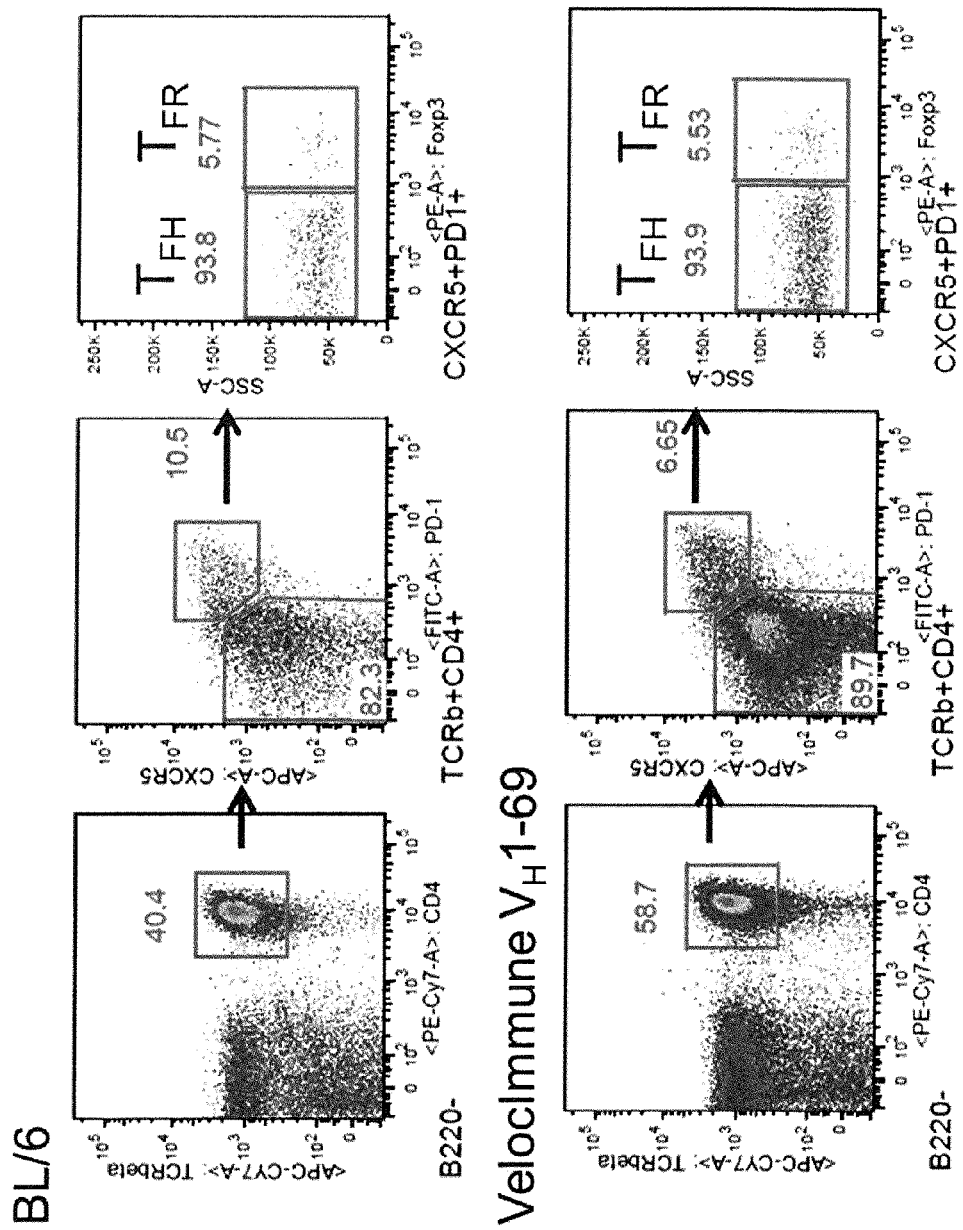
FIG. 4 shows normal T cell development and myeloid cell development of immune cells in VELOCIMMUNE® humanized mice. Top panel: BL/6 wild-type mice; Bottom panel: a $V_H$ restricted VELOCIMMUNE® humanized mouse with a single $V_H$1-9 gene segment replacing all endogenous mouse $V_H$ gene segments. $T_{FH}$: B220$^-$ TCRβ$^+$ CD4$^+$CXCR5$^+$PD-1$^+$Foxp3$^-$; $T_{FR}$: B220$^-$TCRβ$^+$CD4$^+$ CXCR5$^+$PD-1$^+$Foxp3$^+$.
Figure 5A:
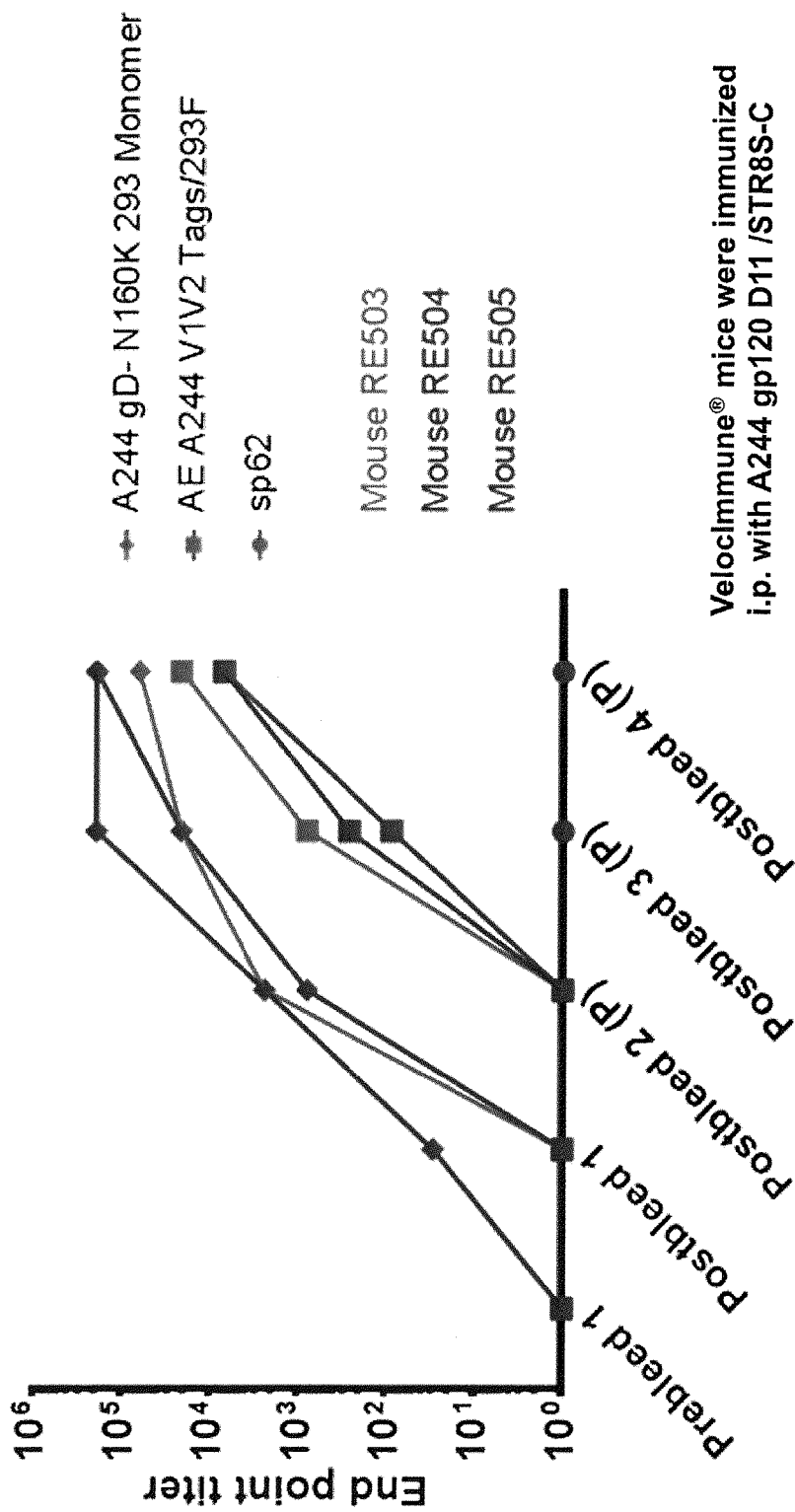
FIG. 5A shows plasma anti HIV-1 Envelope responses of VELOCIMMUNE® humanized mice to immunization with the HIV Envelope AE. A244 gp120 protein (Alam, S. M. et al. (2013) Antigenicity and Immunogenicity of RV144 Vaccine AIDSVAX Clade E Envelope Immunogen Is Enhanced by a gp120 N-Terminal Deletion, J. Viral. 87: 1554-68).
Figure 5B:
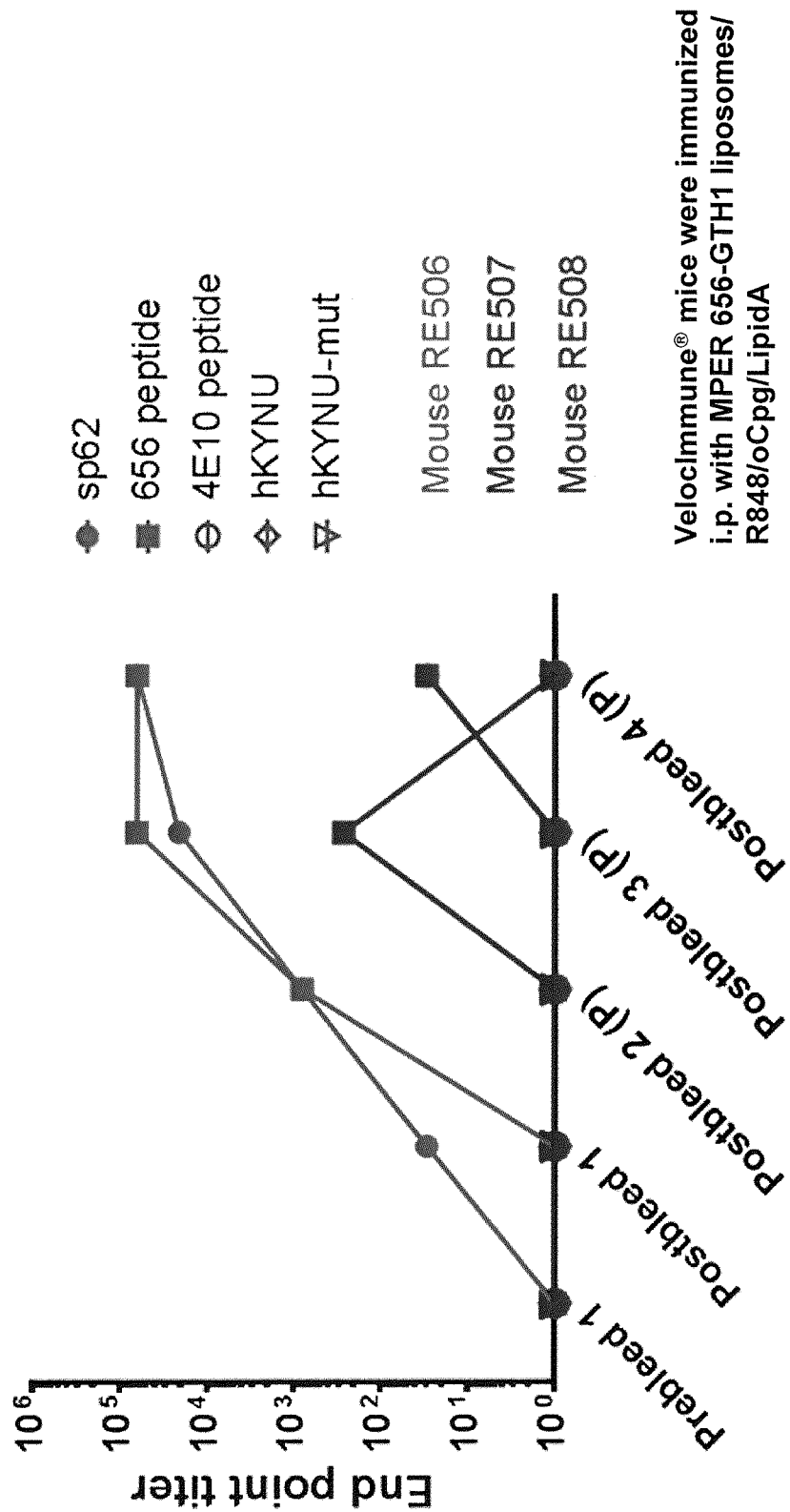
FIG. 5B shows plasma anti HIV-1 Envelope responses of VELOCIMMUNE® humanized mice to immunization with the gp41 membrane proximal external region (MPER) liposome antigen. The plotted lines, from left to right, reflect Mouse RE506, Mouse RE506, Mouse RE507, and Mouse RE508. VELOCIMMUNE® humanized mice were immunized i.p. with MPER 656-GTH1 liposomes/R848/oCpg/ LipidA.
Figure 6:
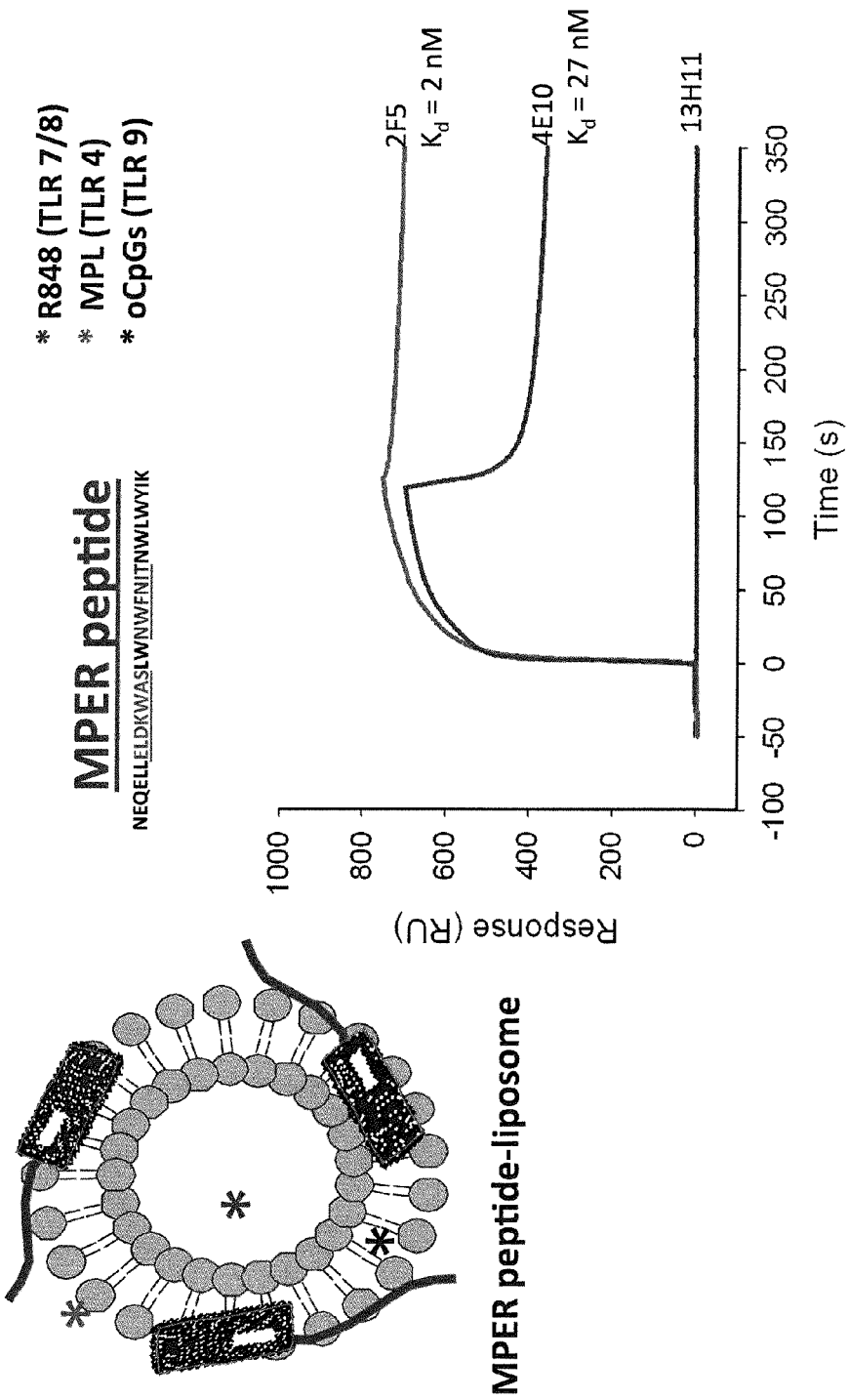
FIG. 6 shows a schema of the gp41 MPER liposome-peptide immunogen (to the left) used in FIG. 5, containing the neutralizing epitopes for the HIV-1 broadly neutralizing antibodies 2F5 and 4E10 (Dennison, S. M. et al., (2009) Stable Docking of Neutralizing Human Immunodeficiency Virus Type 1 gp41 Membrane-Proximal External Region Monoclonal Antibodies 2F5 and 4E10 Is Dependent on the Membrane Immersion Depth of Their Epitope Regions, J. Virol, 83:10211-10223). Top curve.
Figure 7:
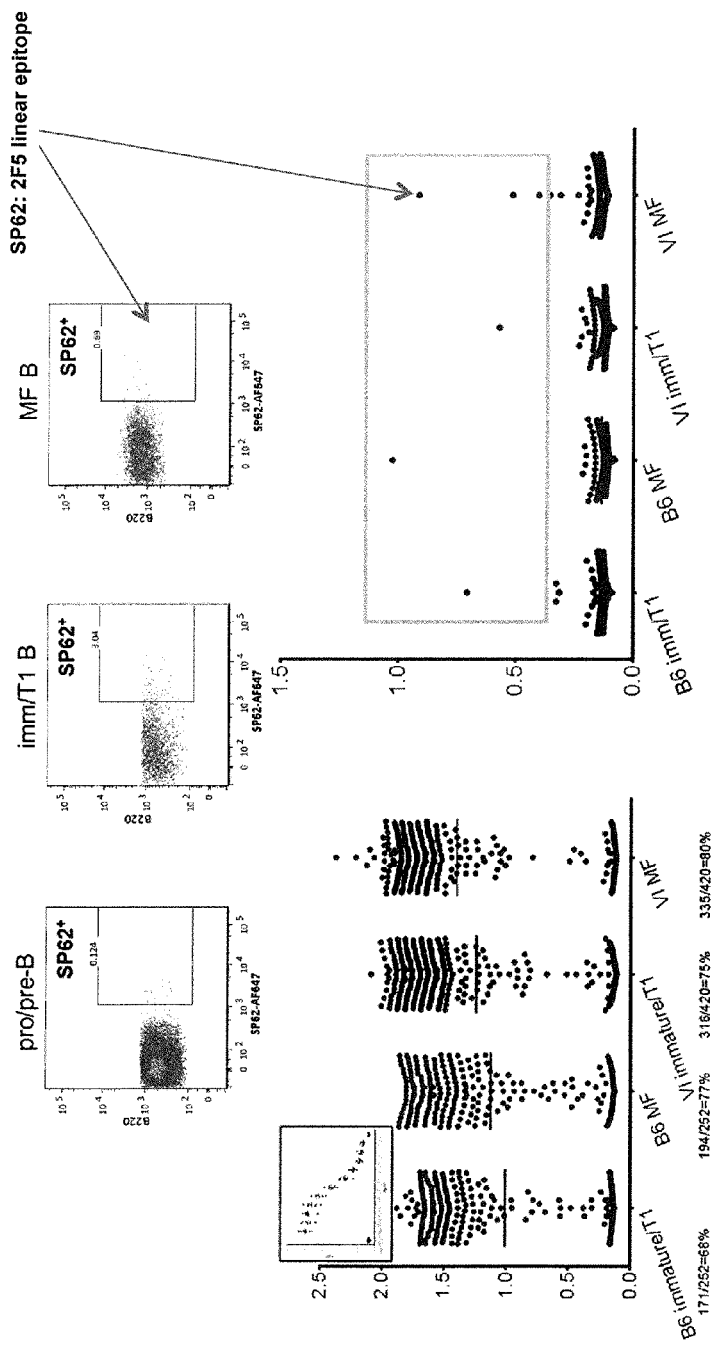
FIG. 7 shows the ability to use a B cell tetramer reflective of the gp41 2F5 MPER neutralizing epitope (Verkoczy, L et al. (2009) Functional, Non-Clonal IgM$^a$-Restricted B Cell Receptor Interactions with the HIV-1 Envelope gp41 Membrane Proximal External Region, PLoS One 4(10): e7215, 2009) to identify and isolate naïve B cell precursors of this lineage from pre-immune VELOCIMMUNE® humanized mice.

The term "broad spectrum antibody" as used herein includes antibodies produced by B cells that can bind a plurality of epitopes or antigenic determinants of an antigen. In one embodiment, the broad spectrum antibody possesses polyreactivity against various epitopes or antigenic determinants. In one embodiment, the broad spectrum antibody includes autoreactive antibodies expressed by ancestral B cells, immatuare autoreactive B cells, or intermediate B cells.

The term "broadly neutralizing antibody" as used herein includes antibodies produced by B cells that neutralize diverse strains of a particular infectious agent or a pathogen.

The term "the unmutated ancestor antibody" or "UA" as used herein includes antibodies expressed by a naïve B cell. In one embodiment, the unmutated ancestor antibody is displayed on an early B cell as an IgM antibody. In one embodiment, the unmutated ancestor antibody comprises a rearrangement of germline gene segments prior to class switching.

The term "intermediate antibodies" or "IA" used herein includes antibodies made by intermediates in the clonal lineage generated by affinity maturation of a naïve B cell in a germinal center.

The term "germinal center" as used herein includes a location in immune tissues at which dendritic and other cells present B cell contact antigen, helper T cells make contact with B cells, and immunoglobulin class switching and somatic hypermutation take place.

Methods and compositions using B Cell Lineage Immunogen Design in non-human animals comprising a humanized immunoglobulin locus (e.g., the VELOCIMMUNE® humanized mouse) for iterative development of vaccine immunogens for infectious diseases. This can be accomplished by use of infectious disease agent components as antigen-specific labels to identify precursors of protective antibodies in unimmunized or uninfected VELOCIMMUNE® humanized mice or using similar reagents and related strategies to identify immunogen-induced clonal lineages of anti-infectious agent antibodies that are developing in the desired direction, and then producing these antibodies to use as templates for iterative vaccine design, an end goal of which is to identify a series of novel immunogens to drive an otherwise subdominant or disfavored B cell maturation pathway to become dominant, and therefore produce sufficient plasma and tissue levels of antibody to be protective in the setting of vaccination.

A number of infectious diseases are characterized as having regions of the outer coats, envelopes or virion spikes to which neutralizing antibodies can be made, but for a variety of reasons, are not routinely made. Examples of these infections include HIV-1, Hepatitis C, influenza and dengue (reviewed in Haynes, B F et al. (2012) B-cell-lineage immunogen design in vaccine development with HIV-1 as a case study, Nature Biotech 30:423-433). A strategy for overcoming many of the road-blocks in induction of such protective anti-infectious agent antibodies has been proposed termed B Cell Lineage Immunogen Design, in which clonal lineages of rare desired antibodies are isolated, recombinantly expressed, and used as templates for vaccine design.

The VELOCIMMUNE® humanized mouse represents the most advanced form of mice that carry humanized Ig loci. The full complement of human $V_H$, Vκ, D, $J_H$ and Jκ gene segments replace the endogenous loci. VELOCIMMUNE® humanized mice are capable of class-switch recombination, somatic hypermuation, and affinity-driven selection in germinal centers—thus they are and excellent and unique model to rapidly vaccinate or select pre-vaccination naïve precursors for use with B cell lineage immunogen design to design novel immunogens for infectious agent vaccine development. VELOCIMMUNE® humanized mice that selectively express a limited $V_H$ repertoire, or only one human $V_H$ (such as $V_H$1-69 as just one representative example), can also advantageously be used for this purpose.

The VELOCIMMUNE® humanized mice can be used in two ways for design of vaccine immunogens. First, pre-immune unvaccinated mouse bone marrow can be used to isolate antigen-specific naïve B cells that bind to antigen-specific infectious agent reagents bearing broad neutralizing epitopes, the antibodies reflective of the naïve B Cell Receptors (BCR) isolated and made recombinantly, and then immunogens selected for their high affinity binding to these BCR in order to discover immunogens that would selectively drive desired broad neutralizing B cell lineages to mature in peripheral lymph nodes and spleen. Second, VELOCIMMUNE® humanized mice can also be vaccinated with existing immunogens that themselves are antigenic for the broad neutralizing antibodies one is trying to induce, and the antibodies induced are then isolated by making monoclonal antibodies from the spleens or lymph nodes of the immunized mice, the antibodies made recombinantly, and then the most mature antibodies in the desired lineage used as a template to further drive the desired lineage to full expression of the desired function, e.g., a protective effector function against an infectious agent. That protective function can include virus neutralization, antibody-dependent cellular cytotoxicity against infectious agent-infected cells, prevention of movement of infectious agent across mucosal barriers, and blocking of entry of infectious agent in cell targets.

Thus, the described processes can identify immunogens by iterative design based on using VELOCIMMUNE® humanized mouse-derived antibodies as templates for novel vaccine components.

Failed immunization of humans with human pathogen envelopes or epitopes presents a major public health challenge. Human immune systems are not always able to develop broadly neutralizing antibodies against human pathogens, including some of the most clinically important pathogens. Many reasons exist for these difficulties (reviewed in Haynes, B. et al. (2012) B-cell-lineage immunogen design in vaccine development with HIV-1 as a case study, Nature Biotech. 30(5):423-433). Whatever the reasons, it is clear that better and more useful systems for manipulation immune cells to develop more broadly neutralizing antibodies against clinically important antigens are in great need. In particular, powerful non-human systems for manipulating the development and design of B cell clones are in great need.

Because antibodies are ultimately derived from B cells that have (usually) undergone extensive selection, a detailed understanding of B cell ontogeny, and crucial junctures in B cell development, are necessary to develop useful clonal B cell lines that express broadly neutralizing antibodies. Just as important as an understanding of the fine details of B cell ontogeny is the availability of a system that can be manipulated to extract the benefits of our understanding of B cell ontology. Rodents with humanized immunoglobulin loci, which generate B cells that express antibodies with human sequences, may be useful. Currently, the best candidate system is the Regeneron VELOCIMMUNE® humanized mouse, which comprises a replacement at the endogenous mouse unrearranged heavy chain locus with the human unrearranged heavy chain locus; and a replacement of the endogenous mouse unrearranged κ variable gene locus with the human unrearranged κ light chain locus; wherein the human unrearranged loci are operably linked to endogenous mouse constant regions. See, e.g., U.S. Pat. No. 7,105,348, U.S. Pat. No. 6,596,541, US Pat. Appl. Publ. Nos. 2007/0061900, 2011/0258710, 2011/0283376, 2012/0322108; each hereby incorporated by reference. Non-human animals with restricted heavy chain loci, e.g., $V_H$1-69 mice, may also be used; see, e.g., U.S. Ser. No. 13/653,456, hereby incorporated by reference.

Compositions and methods are provided for developing vaccine immunogens using animals that comprise humanized immunoglobulin loci. Non-human animals (e.g., rodents, e.g., mice and rats) that are genetically modified to comprise human immunoglobulin variable domains and/or human unrearranged heavy chain variable gene segments and unrearranged light chain variable gene segments (e.g., κ, λ, or κ and λ) are used in a process to design vaccines, or vaccine candidates.

Varieties of Non-Human Animals with Humanized Immunoglobulin Loci

In various aspects, suitable humanized non-human animals for generating B cells for use in the methods described herein include, for example, VELOCIMMUNE® humanized mice as described in, e.g., US 20012/0322108A1, US 2007/0061900A1, US 2011/0258710A1, US 2001/0283376A1, U.S. Pat. No. 6,596,541, U.S. Pat. No. 7,105, 248, each hereby incorporated by reference. Other suitable non-human animals include, for example, non-human animals comprising a limited heavy chain repertoire are described in U.S. Ser. No. 13/653,456, filed 17 Oct. 2012; as well as non-human animals disclosed in U.S. Ser. No. 61/658,466, filed 12 Jun. 2012, and U.S. Ser. No. 61/663, 131, filed 22 Jun. 2012; each application and patent incorporated herein by reference.

Advantages of VELOCIMMUNE® humanized mice include that they exhibit normal variable region usage and junctional diversity, normal somatic hypermutation, normal numbers and distribution of B cells in spleen and lymph node, normal B cell differentiation in bone marrow, normal allelic exclusion, normal κλ light chain ratios, normal serum levels for all Ig isotypes (IgM, IgG1, IgG2a, IgG2b, IgG3, IgE, IgA), normal immune responses to target antigens, and normal ability to generate stable, wherein "normal" refers to identical wild-type mouse littermates. Most, if not all, of these unique features of VELOCIMMMUNE® humanized mice are important for optimal B-cell-lineage immunogen design for vaccine development. VELOCIMMUNE® humanized mice (with restricted or non-restricted heavy chain variable loci) are outstanding platforms for B-cell-lineage immunogen design for vaccine development at least in part because they are an excellent source of bone marrow B cell precursors that reflect the naïve human repertoire, a highly desired reagent for immunogen design (see, e.g., FIG. 1, antibody UA (unmutated antibody), as well as an excellent source of intermediate ancestor antibodies (see, e.g., FIG. 1 at IA1, IA2, IA3), which can be readily primed and boosted to manipulate human variable domain-expressing intermediate ancestor antibodies.

The VELOCIMMUNE® humanized mice (those used herein without a restricted repertoire) comprise a replacement of endogenous mouse V, D, and J gene segments with the full human repertoire of functional V, D, and J segments, operably linked to the mouse heavy chain locus. The VELOCIMMUNE® humanized mice (those used herein without a restricted repertoire) also comprise a replacement of endogenous mouse κ V and J gene segments with the full human repertoire of functional human Vκ and Jκ gene segments.

Non-Human Animals with Restricted Heavy Chain Repertoires: $V_H1$-69 and Beyond

VELOCIMMUNE® humanized mice with restricted repertoires, e.g., the $V_H1$-69 mouse used herein, comprises a replacement at the endogenous mouse locus of all functional mouse heavy chain V, D, and J segments with a single human $V_H1$-69 gene segment (present without polymorphs) operably linked to a plurality of human D segments and a plurality of human J segments, which are operably linked to an endogenous mouse immunoglobulin heavy chain locus.

The restricted heavy chain repertoire mouse is a useful tool in certain circumstances, such as here, to generate clonal lines of B cells that can be used in immunogen design in vaccine development, for it is well-known that certain human gene segments exhibit enhanced usage as against certain infectious agents or pathogens.

$V_H1$-69-derived heavy chains have been observed in a variety of antigen-specific antibody repertoires of therapeutic significance. For instance, $V_H1$-69 was frequently observed in heavy chain transcripts of an IgE repertoire of peripheral blood lymphocytes in young children with atopic disease (Bando et al. (2004) Characterization of $V_H\epsilon$ gene expressed in PBL from children with atopic diseases: detection of homologous $V_H1$-69 derived transcripts from three unrelated patients, Immunology Letters 94:99-106). $V_H1$-69-derived heavy chains with a high degree of somatic hypermutation also occur in B cell lymphomas (Perez et al., (2009) Primary cutaneous B-cell lymphoma is associated with somatically hypermutated immunoglobulin variable genes and frequent use of $V_H1$-69 and $V_H4$-59 segments, British Journal of Dermatology 162:611-618), whereas some $V_H1$-69-derived heavy chains with essentially germline sequences (i.e., little to no somatic hypermutation) have been observed among autoantibodies in patients with blood disorders (Pos et al. (2008) $V_H1$-69 germline encoded antibodies directed towards ADAMTS13 in patients with acquired thrombotic thrombocytopenic purpura, Journal of Thrombosis and Haemostasis 7:421-428).

Further, neutralizing antibodies against viral antigens such as HIV, influenza and hepatitis C (HCV) have been found to utilize germline and/or somatically mutated $V_H1$-69-derived sequences (Miklos et al., (2000) Salivary gland mucosa-associated lymphoid tissue lymphoma immunoglobulin $V_H$ genes show frequent use of $V_H1$-69 with distinctive CDR3 features, Blood 95(12):3878-3884; Kunert et al. (2004) Characterization of molecular features, antigen-binding, and in vitro properties of IgG and IgM variants of 4E10, an anti-HIV type I neutralizing monoclonal antibody, Aids Research and Human Retroviruses 20(7):755-762; Chan et al. (2001) $V_H1$-69 gene is preferentially used by hepatitis C virus-associated B cell lymphomas and by normal B cells responding to the E2 viral antigen, Blood 97(4):1023-1026; Carbonari et al., (2005) Hepatitis C virus drives the unconstrained monoclonal expansion of $V_H1$-69-expressing memory B cells in type II cryoglobulinemia: A model of infection-driven lymphomagenesis, Journal of Immunology 174:6532-6539; Wang and Palese (2009) Universal epitopes of influenza virus hemagglutinins?, Nature Structural & Molecular Biology 16(3):233-234; Sui et al. (2009) Structural and functional bases for broad-spectrum neutralization of avian and human influenza A viruses, Nature Structural & Molecular Biology 16(3):265-273; Marasca et al. (2001) Immunoglobulin Gene Mutations and Frequent Use of $V_H1$-69 and $V_H4$-34 Segments in Hepatitis C Virus-Positive and Hepatitis C Virus-Negative Nodal Marginal Zone B-Cell Lymphoma, Am. J. Pathol. 159(1): 253-261).

However, these are just non-limiting examples of non-human animals that can be used as a platform for making B cell clones. Other humanized rodents can be used to generate B cell populations as well, including systems that employ fully human trangenes or chimeric human variable/non-human constant transgenes, whether the non-human animals be mice, rats, or other non-human animals, e.g., other rodents. Further, suitable humanized non-human animals can comprise a full or a partial repertoire of heavy and/or light chain gene segments. In various aspects, all that is desired is the ability of the non-human animal to develop a B cell clone expressing a variable domain that is broadly neutralizing (or binds the pathogen of interest with sufficiently desirable characteristics, e.g., high avidity, high specificity, etc.) that can be further developed to exhibit desired characteristics.

Thus, the non-human animals (e.g., rodents, e.g., mice or rats) described herein are useful in methods of vaccine design as against human pathogens, based on B cell lineage design methods described herein.

In one aspect, the non-human animal (e.g., a rodent, e.g., a mouse or rat) comprising a modified endogenous non-human immunoglobulin heavy chain locus is provided, comprising a replacement of all functional V gene segments with a single human V gene segment (or a single human V gene segment present in multiple polymorphic forms or copy number), wherein the non-human immunoglobulin heavy chain locus is incapable of rearrangement to form a heavy chain variable gene that is derived from a V gene segment other than the single human V gene segment (or one of the polymorphic forms or copies).

In one embodiment, the single human V gene segment is $V_H1$-69. In one embodiment, the single human V gene segment is $V_H1$-2.

In one embodiment, the locus comprises at least one human or non-human $D_H$ gene segment, and one human or non-human $J_H$ gene segment. In a specific embodiment, the locus comprises a human $D_H$ gene segment and a human $J_H$ gene segment. In a specific embodiment, the locus comprises a human $J_H$ gene segment. In another specific embodiment, the locus comprises a human $V_H1$-69 gene segment (present as a single copy or multiple copies of different polymorphic variants), all functional human $D_H$ gene segments, and all functional human $J_H$ gene segments. In another specific embodiment, the locus comprises a human $V_H1$-2 gene segment (present as a single copy or multiple copies of different polymorphic forms), all functional human $D_H$ gene segments, and all functional human $J_H$ gene segments. In one embodiment, the human V, D, and J gene segments (or V and J gene segments) are operably linked to a mouse constant region gene at an endogenous mouse heavy chain locus. In a specific embodiment, the mouse heavy chain locus comprises a wild-type repertoire of mouse immunoglobulin constant region sequences.

In one aspect, a non-human animal (e.g., a rodent, e.g., a mouse or rat) comprising a modified immunoglobulin heavy chain locus is provided that comprises a heavy chain V segment repertoire that is restricted with respect to the identity of the V segment, and that comprises one or more D segments and one or more J segments, or one or more J segments. In one embodiment, the heavy chain V segment is a human segment. In one embodiment, the one or more D segments are human D segments. In one embodiment, the one or more J segments are human J segments. In one embodiment, the one or more D segments and one or more J segments are human D and human J segments.

In one embodiment, the modified locus is a non-human locus. In one embodiment, the non-human locus is modified with at least one human immunoglobulin sequence.

In one embodiment, the restriction is to one V segment family member. In one embodiment, the one V segment family member is present in two or more copies. In one embodiment, the one V segment family member is present as two or more variants (e.g., two or more polymorphic forms of the V segment family member). In one embodiment, the one V segment is a human V segment family member. In one embodiment, the one V segment family member is present in a number of variants as is observed in the human population with respect to that variant.

In one embodiment, the restriction is to a human $V_H1$-69 gene segment. In one embodiment, the human $V_H1$-69 gene segment is present in two or more copies. In one embodiment, the human $V_H1$-69 gene segment is present as two or more variants (e.g., two or more polymorphic forms the human $V_H1$-69 gene). In one embodiment, the human $V_H1$-69 gene segment is present in a number of variants as is observed in the human population with respect to the human $V_H1$-69 gene segment.

In one embodiment, the restriction is to a human $V_H1$-2 gene segment. In one embodiment, the human $V_H1$-2 gene segment is present in two or more copies. In one embodiment, the human $V_H1$-2 gene segment is present as two or more variants (e.g., two or more polymorphic forms the human $V_H1$-2 gene). In one embodiment, the human $V_H1$-2 gene segment is present in a number of variants as is observed in the human population with respect to the human $V_H1$-2 gene segment.

In one aspect, a non-human animal comprising a humanized heavy chain variable immunoglobulin locus is provided that comprises a single functional human V segment. In one embodiment, the single functional human V segment is selected from a $V_H1$-2, $V_H1$-3, $V_H1$-8, $V_H1$-18, $V_H1$-24, $V_H1$-45, $V_H1$-46, $V_H1$-58, $V_H1$-69, $V_H2$-5, $V_H2$-26, $V_H2$-70, $V_H3$-7, $V_H3$-9, $V_H3$-11, $V_H3$-13, $V_H3$-15, $V_H3$-16, $V_H3$-20, $V_H3$-21, $V_H3$-23, $V_H3$-30, $V_H3$-30-3, $V_H3$-30-5, $V_H3$-33, $V_H3$-35, $V_H3$-38, $V_H3$-43, $V_H3$-48, $V_H3$-49, $V_H3$-53, $V_H3$-64, $V_H3$-66, $V_H3$-72, $V_H3$-73, $V_H3$-74, $V_H4$-4, $V_H4$-28, $V_H4$-30-1, $V_H4$-30-2, $V_H4$-30-4, $V_H4$-31, $V_H4$-34, $V_H4$-39, $V_H4$-59, $V_H4$-61, $V_H5$-51, $V_H6$-1, $V_H7$-4-1, and a $V_H7$-81 segment. In one embodiment, the single functional human V segment is a $V_H1$-69 segment; in a specific embodiment, the single functional human V segment is present in 1, 2, 3, 4, 5, 6, 7, 8, 9, 10, 11, 12, or 13 polymorphic forms found in the human population. In one embodiment, the single functional human V segment is a $V_H1$-2 segment; in a specific embodiment, the single functional human V segment is present in 1, 2, 3, 4, or 5 polymorphic forms found in the human population.

In one aspect, a non-human animal comprising a restricted immunoglobulin heavy chain V gene segment repertoire is provided, wherein the non-human animal further comprises one or more human immunoglobulin κ light chain variable segments (Vκ). In one embodiment, the one or more Vκ segments are operably linked to one or more human J segments. In a specific embodiment, the J segments are human Jκ segments. In another specific embodiment, the non-human animal does not express an immunoglobulin λ light chain. In another specific embodiment, the non-human animal does not comprise a functional human or functional endogenous immunoglobulin λ light chain variable locus.

In one embodiment, the non-human animal is a rodent. In one embodiment, the rodent is selected from a mouse and a rat.

In one embodiment, the non-human animal comprises a replacement at the endogenous non-human immunoglobulin Vκ locus of all or substantially all functional endogenous Vκ segments with one or more functional human Vκ segments. In a further specific embodiment, the replacement is with all or substantially all functional human immunoglobulin Vκ segments.

In one embodiment, the non-human animal comprises a replacement at the endogenous non-human immunoglobulin Vκ locus of all or substantially all functional endogenous Vκ gene segments with human Vκ gene segments selected from Vκ4-1, Vκ5-2, Vκ7-3, Vκ2-4, Vκ1-5, Vκ1-6, Vκ3-7, Vκ1-8, Vκ1-9, Vκ2-10, Vκ3-11, Vκ1-12, Vκ1-13, Vκ2-14, Vκ3-15, Vκ1-16, Vκ1-17, Vκ2-18, Vκ2-19, Vκ3-20, Vκ6-21, Vκ1-22, Vκ1-23, Vκ2-24, Vκ3-25, Vκ2-26, Vκ1-27, Vκ2-28, Vκ2-29, Vκ2-30, Vκ3-31, Vκ1-32, Vκ1-33, Vκ3-34, Vκ1-35, Vκ2-36, Vκ1-37, Vκ2-38, Vκ1-39, Vκ2-40, and a combination thereof.

In one embodiment, the non-human animal comprises a replacement at the endogenous non-human immunoglobulin Jκ locus of all or substantially all functional endogenous non-human immunoglobulin Jκ segments with one or more functional human immunoglobulin Jκ segments. In a further specific embodiment, the replacement is with all or substantially all functional human immunoglobulin Jκ segments.

In one embodiment, the non-human animal comprises a replacement at the endogenous non-human immunoglobulin Jκ locus of all or substantially all functional endogenous non-human immunoglobulin Jκ gene segments with human Jκ gene segments selected from Jκ1, Jκ2, Jκ3, Jκ4, Jκ5, and a combination thereof.

In a specific embodiment, the non-human animal comprises an immunoglobulin heavy chain variable region locus that comprises a repertoire of V segments consisting essentially of a single V segment and/or polymorphic variants thereof. In one embodiment, the single immunoglobulin heavy chain V segment is a human $V_H$1-69 segment, and the non-human animal further comprises a replacement of all functional non-human $D_H$ segments with all functional human $D_H$ segments, and further comprises a replacement of all functional non-human $J_H$ segments with all functional human $J_R$ segments, and wherein the immunoglobulin heavy chain variable region locus is operably linked to a human or non-human constant region gene sequence. In a specific embodiment, the constant region gene sequence is an endogenous non-human constant region gene sequence. In a specific embodiment, the non-human animal rearranges segments at the non-human immunoglobulin heavy chain locus to form a gene encoding heavy chain variable region comprising a human $V_H$1-69 sequence, a human $D_H$ sequence, a human $J_H$ sequence, and a mouse constant region sequence.

In a specific embodiment, the non-human animal comprises an immunoglobulin heavy chain variable region locus that comprises a repertoire of V segments consisting essentially of a single V segment and/or polymorphic variants thereof. In one embodiment, the single immunoglobulin heavy chain V segment is a human $V_H$1-2 segment, and the non-human animal further comprises a replacement of all functional non-human $D_R$ segments with all functional human $D_H$ segments, and further comprises a replacement of all functional non-human $J_H$ segments with all functional human $J_H$ segments, and wherein the immunoglobulin heavy chain variable region locus is operably linked to a human or non-human constant region gene sequence. In a specific embodiment, the constant region gene sequence is an endogenous non-human constant region gene sequence. In a specific embodiment, the non-human animal rearranges segments at the non-human immunoglobulin heavy chain locus to form a gene encoding heavy chain variable region comprising a human $V_H$1-2 sequence, a human $D_H$ sequence, a human $J_H$ sequence, and a mouse constant region sequence.

In one aspect, a non-human animal comprising a restricted immunoglobulin heavy chain V segment repertoire is provided, wherein the non-human animal comprises one or more human λ light chain variable (Vλ) segments. In one embodiment, the one or more human Vλ segments are operably linked to one or more human J segments. In a specific embodiment, the J segments are human Jλ segments. In another specific embodiment, the non-human animal does not express a κ light chain. In another specific embodiment, the non-human animal does not comprise a functional human or non-human κ light chain variable locus.

In one embodiment, the non-human animal further comprises a replacement of all or substantially all functional non-human immunoglobulin In one embodiment, the non-human animal comprises a replacement of all or substantially all functional non-human immunoglobulin Vλ segments with one or more functional human immunoglobulin Vλ segments. In a further specific embodiment, the replacement is with all or substantially all functional human immunoglobulin Vλ segments.

In one embodiment, the non-human animal comprises a replacement of all or substantially all functional non-human Vλ segments with a fragment of cluster A of the human λ light chain locus. In a specific embodiment, the fragment of cluster A of the human λ light chain locus comprises human Vλ gene segments Vλ3-27 through Vλ3-1.

In one embodiment, the non-human animal comprises a replacement of all or substantially all functional non-human Vλ segments with a fragment of cluster B of the human λ light chain locus. In a specific embodiment, the fragment of cluster B of the human λ light chain locus comprises human Vλ gene segments Vλ5-52 through Vλ1-40.

In one embodiment, the non-human animal comprises a replacement of all or substantially all functional non-human Vλ segments with a fragment of cluster A and a fragment of cluster B of the human light chain locus, wherein as a result of the replacement comprise human Vλ gene segments Vλ5-52 through Vλ3-1.

In one embodiment, the non-human animal comprises a replacement of all or substantially all functional non-human Vλ segments with at least 12 human Vλ gene segments, at least 28 human Vλ gene segments, or at least 40 human Vλ gene segments.

In one embodiment, the non-human animal comprises a replacement of all or substantially all functional non-human immunoglobulin Jλ gene segments with one or more functional human immunoglobulin Jλ gene segments. In a further specific embodiment, the replacement is with all or substantially all functional human immunoglobulin Jλ gene segments. In various embodiments, the functional human Jλ gene segments include Jλ1, Jλ2, Jλ3 and Jλ7.

In a specific embodiment, the non-human animal comprises an immunoglobulin heavy chain variable ($V_H$) region locus that comprises only a single $V_H$ segment, wherein the single $V_H$ segment is a human $V_H$1-69 segment or a human $V_H$1-2 segment, and further comprises a replacement of all functional non-human $D_H$ segments with all functional human $D_H$ segments, and further comprises a replacement of all functional non-human $J_H$ segments with all functional human $J_H$ segments, and wherein the $V_H$ region locus is operably linked to a human or non-human constant region gene sequence. In a specific embodiment, the constant region gene sequence is a non-human constant region gene sequence, e.g., an endogenous non-human constant gene sequence. In a specific embodiment, the non-human animal rearranges segments at the non-human immunoglobulin heavy chain locus to form a gene encoding an immunoglobulin heavy chain variable region comprising a human $V_H$1-69 sequence (or a human $V_H$1-2 sequence), a human $D_H$ sequence, a human $J_H$ sequence, and an endogenous non-human constant region sequence.

We claim:

1. A method for screening for a broad spectrum antibody against an antigen of interest from a pathogen, which is HIV, influenza or hepatitis C, comprising:
    (a) administering a first immunogen derived from the antigen of interest to a mouse from a mouse line comprising in its germline:
        (i) a restricted immunoglobulin heavy chain locus comprising a single human unrearranged $V_H$ gene segment, which is a human $V_H$1-69 gene segment or polymorphic variant thereof, one or more human $D_H$ gene segments, and one or more human $J_H$ gene segments operably linked to a heavy chain constant region nucleic acid sequence,
        (ii) a genetically modified immunoglobulin light chain locus comprising one or more human $V_K$ gene segments and one or more human $J_K$ gene segments, wherein the $V_K$ and the $J_K$ gene segments are operably linked to a light chain constant region nucleic acid sequence, and wherein the first immunogen comprises a plurality of epitopes;

(b) allowing the mouse to mount an immune response against the first immunogen, wherein the immune response comprises generation of non-human B cells that express human immunoglobulin heavy chain (IgH) VDJ and human immunoglobulin light chain (IgL) VJ sequences;

(c) isolating clonally related B cells from the mouse that express a B cell receptor (BCR) that specifically binds a first epitope of the first immunogen;

(d) obtaining IgH VDJ and IgL VJ amino acid sequences expressed by the B cell receptor (BCR) of the clonally related B cells;

(e) deducing from the IgH VDJ and IgL VJ sequences unmutated B cell receptor (BCR) VDJ and VJ amino acid sequences; and one or more intermediate ancestor B cell receptor (BCR) VDJ and VJ amino acid sequences expressed by B cells at an intermediate stage of differentiation;

(f) providing a plurality of second immunogens comprising second epitopes distinct from the first epitope that bind with enhanced affinity to the unmutated B cell receptor (BCR) or the intermediate ancestor B cell receptor (BCR) relative to the first immunogen;

(g) serially administering to another mouse of the line second immunogens selected from the plurality of the second immunogens in (f), the serial administration starting with a second immunogen to the unmutated BCR and following with second immunogens to intermediate BCRs successively more distant phylogenically from the unmutated BCR; and (h) determining whether the immune response from the mouse of (g) includes a broad spectrum antibody, which binds a plurality of the second epitopes.

2. The method of claim 1, wherein the first and second immunogens of steps (a) and (g) are administered as a liposomal complex.

3. The method of claim 1, wherein the antigen of interest is, or is derived from, an infectious agent or a pathogen, and the broad spectrum antibody is a broadly neutralizing antibody against the infectious agent or the pathogen.

4. The method of claim 1, wherein all, or substantially all, functional endogenous $V_H$, $D_H$, and $J_H$ gene segments in the immunoglobulin heavy chain locus have been deleted or rendered non-functional.

5. The method of claim 4, wherein the restricted immunoglobulin heavy chain locus comprises an endogenous Adam6a gene, Adam6b gene, or both, and the genetic modification in the heavy chain locus does not affect the expression or function of the endogenous Adam6a gene, Adam6b gene, or both.

6. The method of claim 4, wherein the mouse comprises an ectopically present Adam6a gene, Adam6b gene, or both.

7. The method of claim 1, wherein the heavy or light chain constant region nucleic acid sequence is a human or a rodent nucleic acid sequence.

8. The method of claim 1, wherein the constant region nucleic acid sequence is a mouse constant region nucleic acid sequence.

9. The method of claim 1, wherein all, or substantially all, functional endogenous $V_H$, $D_H$, and $J_H$ gene segments in the immunoglobulin heavy chain locus have been rendered non-functional, and the human $V_H$, $D_H$, and $J_H$ gene segments are present on a transgene.

10. The method of claim 1, where the human $V_H$, $D_H$, and $J_H$ gene segments are operably linked to an endogenous constant region nucleic acid sequence at an endogenous non-human immunoglobulin heavy chain locus.

11. The method of claim 1, wherein the genetically modified immunoglobulin light chain locus comprises a replacement of all, or substantially all, functional $V_K$ gene segments and $J_K$ gene segments with one or more human $V_K$ gene segments and one or more human $J_K$ segments, wherein the human $V_K$ gene segments and the human $J_K$ gene segments are operably linked to a light chain constant region nucleic acid sequence.

12. The method of claim 1, wherein the mouse comprises a replacement at the endogenous non-human immunoglobulin $V_K$ locus of all or substantially all functional endogenous $V_K$ gene segments with human $V_K$ gene segments the group consisting of selected from $V_K4-1$, $V_K5-2$, $V_K7-3$, $V_K2-4$, $V_K1-5$, $V_K1-6$, $V_K3-7$, $V_K1-8$, $V_K1-9$, $V_K2-10$, $V_K3-11$, $V_K1-12$, $V_K1-13$, $V_K2-14$, $V_K3-15$, $V_K1-16$, $V_K1-17$, $V_K2-18$, $V_K2-19$, $V_K3-20$, $V_K6-21$, $V_K1-22$, $V_K1-23$, $V_K2-24$, $V_K3-25$, $V_K2-26$, $V_K1-27$, $V_K2-28$, $V_K2-29$, $V_K2-30$, $V_K3-31$, $V_K1-32$, $V_K1-33$, $V_K3-34$, $V_K1-35$, $V_K2-36$, $V_K1-37$, $V_K2-38$, $V_K1-39$, $V_K2-40$, and a combination thereof.

13. The method of claim 1, wherein the mouse comprises a replacement at the endogenous non-human immunoglobulin $J_K$ locus of all or substantially all functional endogenous non-human immunoglobulin $J_K$ gene segments with human $J_K$ gene segments selected from $J_K1$, $J_K2$, $J_K3$, $J_K4$, $J_K5$, and a combination thereof.

14. The method of claim 11, wherein the one or more human $V_K$ and $J_K$ segments are operably linked to an endogenous light chain constant region nucleic acid sequence at an endogenous non-human locus.

* * * * *

UNITED STATES PATENT AND TRADEMARK OFFICE
CERTIFICATE OF CORRECTION

PATENT NO. : 9,963,501 B2
APPLICATION NO. : 14/174563
DATED : May 8, 2018
INVENTOR(S) : Barton Haynes et al.

Page 1 of 1

It is certified that error appears in the above-identified patent and that said Letters Patent is hereby corrected as shown below:

On the Title Page

At Item (73):
"(73) Assignee: Regeneron Pharmaceuticals, Inc., Tarrytown, NY (US)"

Should read:
--(73) Assignees: Regeneron Pharmaceuticals, Inc., Tarrytown, NY (US);
                  Duke University, Durham, NC (US)--

Signed and Sealed this
Twenty-third Day of April, 2019

Andrei Iancu
*Director of the United States Patent and Trademark Office*